United States Patent
Langer et al.

(10) Patent No.: US 6,710,217 B1
(45) Date of Patent: Mar. 23, 2004

(54) METHOD FOR PRODUCING 4-CHLOROBIPHENYL AND 4-CHLOROBIPHENYL-SPECIFIC SPECIFICATIONS

(75) Inventors: Reinhard Langer, Tönisvorst (DE); Alexander Klausener, Pulheim (DE); Paul Wagner, Düsseldorf (DE); Lothar Puppe, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/009,536

(22) PCT Filed: May 3, 2000

(86) PCT No.: PCT/EP00/03945

§ 371 (c)(1), (2), (4) Date: Nov. 13, 2001

(87) PCT Pub. No.: WO00/69798

PCT Pub. Date: Nov. 23, 2000

(30) Foreign Application Priority Data

May 14, 1999 (DE) .......................... 199 22 402

(51) Int. Cl.$^7$ .......................... C07C 17/00; C07C 22/00; C07C 25/00
(52) U.S. Cl. .......................... 570/208; 570/182; 570/207; 570/209; 570/210
(58) Field of Search .................... 570/208, 182, 570/207, 209, 210

(56) References Cited

U.S. PATENT DOCUMENTS

| | | |
|---|---|---|
| 1,835,754 A | 12/1931 | Britton et al. |
| 1,890,427 A | 12/1932 | Britton et al. |
| 4,950,817 A * | 8/1990 | Botta et al. .................. 570/208 |

FOREIGN PATENT DOCUMENTS

FR    2 067 384    8/1971

OTHER PUBLICATIONS

*Botta, Artur et al: "Selective p–chlorination of biphenyl in L–zeolites" Angew. Chem. (1991), 103(12), 1687-9 (see also angew. Chem., Int. Ed. Engl., 1991, 30(12), 1689–90), XP00213809 in der Anmeldung erwahnt das ganze Dokument.

J. Org. Chem., (month unavailable) 1997, 62, pp. 3405–3406, Palladium–Catalyzed Cross–Coupling of Arenediazonium Salts with Arylboronic Acids by S. Sengupta and S. Bhattacharyya.

Nippon Kagaku Kaishi, (month unavailable) 1997, No. 2, pp. 119–126, The Chemical Society of Japan.

Tetrahedron, vol. 52, No. 21, pp. 7201, (month unavailable) 1996, Preparation of Polyfunctional Aryl and Alkenyl Zinc Halides from Functionalized Unsaturated Organolithiums and their Reactivity in Cross–Coupling and Conjugated Addition Reactions by Ingo Klement et al.

J. Org. Chem., (month unavailable) 1992, pp. 391–393, Hypochlorite–Induced Substitution of Chlorine for Bromine in Aromatic Compounds by J. T. Arnold et al.

J. Chem. Research (S), (month available) 1994, pp. 216–217, N–Methyl Quaternisation of 2,5–Diaryl Tetrazoles and Reaction of the Tetrazolium Salts with Ethoxide Base by Richard N. Butler et al.

Tetrahedron, vol. 52, No. 26, pp. 8863–8866, (month unavailable) 1996, Mild Chlorination of Aromatic Compounds with Tin(IV) Choride and Lead Tetraacetate by Hussni A. Muathen.

Ind. Eng. Chem. Res. (month unavailable) 1995, 34, pp. 421–433, Preparing Catalytic Materials by the Sol–Gel Method by D. A. Ward and E. I. Ko.

Chemicky Prusyl. Prague, (month unavailable) 1980, pp. 529–530, Priprava cistych chlorbifenylov by Pavol Lishak and Eva Zemanova.

* cited by examiner

Primary Examiner—Shailendra Kumar
Assistant Examiner—Elvis O. Price
(74) Attorney, Agent, or Firm—Godfried R. Akorli; Diderico van Eyl

(57) ABSTRACT

The invention relates to a process for preparing 4-chlorobiphenyl by
(a) reacting biphenyl and chlorine in the presence of one or more ring-chlorination catalysts, and
(b) subjecting the reaction mixture obtained in step (a) to fractional distillation to obtain 4-chlorobiphenyl.

10 Claims, No Drawings

METHOD FOR PRODUCING 4-CHLOROBIPHENYL AND 4-CHLOROBIPHENYL-SPECIFIC SPECIFICATIONS

This application is a 371 of PCT/EP00/03945, filed May 3, 2000.

The present invention relates to a process for preparing 4-chlorobiphenyl by chlorination of biphenyl, isolation of the 4-chlorobiphenyl from the reaction mixture in high purity and 4-chlorobiphenyl having a low 3-chlorobiphenyl content.

4-Chlorobiphenyl is an important intermediate in the preparation of pharmaceuticals and crop protection products. It is therefore necessary that it can be obtained in a simple manner, inexpensively and in high purities.

Processes for preparing 4-chlorobiphenyl which require relatively complex precursors such as phenylboronic acid, 4-chloro-phenyl-diazonium salts, phenyl-magnesium bromide, 4-bromo-chlorobenzene, 4-iodo-chlorobenzene, phenyl triflate, 4-bromo-biphenyl and diphenyl-tetrazole compounds are known (cf Org. Chem., 62(10), 3405–6 (1997); Nippon Kagaku Kaishi, 1997 (2), 119–26; Tetrahedron, 52(21), 7201–20 (1996); Org. Chem. 57(1), 391–3 (1992) and J. Chem. Res., Synop. 1994 (6), 216–7). Even if the yields are sometimes above 90% and 4-chlorobiphenyl can be isolated readily in pure form and free of 3-chlorobiphenyl, the precursors can be prepared only by very complicated processes. For this reason, these processes for preparing 4-chlorobiphenyl are uneconomical and relatively unsuitable for use on an industrial scale.

Tetrahedron 52(26), 8863–6 (1996) describes the chlorination of biphenyl using 2 equivalents of tin tetrachloride and 1 equivalent of lead tetraacetate. The yield of 4-chlorobiphenyl is 70%. Nothing is said about the amount of 2- and 3-chlorobiphenyl formed and the degree to which they are separated off. The use of large amounts of lead tetraacetate and tin tetrachloride makes the process costly and uneconomical.

Angew. Chem., 103(12), 1687–9 (1991) describes the chlorination of biphenyl catalyzed by zeolites of the structure type LTL, with the potassium form (K-L) being mentioned as being particularly favorable. However, this publication is not directed at the preparation and isolation of 4-chlorobiphenyl, but rather the preparation and isolation of 4,4'-dichlorobiphenyl which can be crystallized from the product mixture.

It would be desirable to be able to prepare 4-chlorobiphenyl in a single step from biphenyl and chlorine. According to U.S. Pat. No. 1,890,427, this is possible by chlorination of biphenyl in chlorobenzene in the presence of metallic iron as catalyst. However, this gives a mixture comprising 4-chlorobiphenyl, 3-chlorobiphenyl, 2-chlorobiphenyl and unreacted biphenyl. The separation of this mixture is very complicated. For separating off one isomer, the reference describes crystallization from noneutectic mixtures above the freezing point of the eutectic. This means that separation of the entire mixture makes it necessary to carry out a complicated sequence of distillation and crystallization steps. Czech. Chem. Prum., 30(10), 529–32 (1980) confirms this. To achieve purities of greater than 99%, the latter reference describes the following steps to be carried out in succession for the separation of mixtures comprising 2-, 3- and 4-chlorobiphenyl: 1. distillation, 2. crystallization of the fractions from the distillation and 3. recrystallization of the fractions from the crystallization from ethanol.

The problems in isolating 4-chlorobiphenyl from reaction mixtures obtained in the chlorination of biphenyl explain why the complicated synthetic route indicated at the outset has been considered for the preparation of pure 4-chlorobiphenyl.

There is therefore still a need for a process which allows 4-chlorobiphenyl to be obtained in high purity in a simple manner from inexpensive starting compounds.

We have now found a process for preparing 4-chlorobiphenyl which is characterized in that biphenyl and chlorine are reacted in the presence of ring-chlorination catalysts and the reaction mixture obtained is subjected to fractional distillation.

Suitable ring-chlorination catalysts are the catalysts known for this purpose, e.g. the anhydrous chlorides of main groups 3, 4 and 5 and of transition groups 3 to 10 of the Periodic Table of the Elements, also the anhydrous chlorides of the rare earths. Preference is given to boron trichloride, aluminum trichloride and iron trichloride. Further suitable catalysts are heterogeneous aluminosilicates, e.g. sheet silicates such as montmorillonite and bentonite, heterogeneous aluminosilicates having amorphous, vitreous porous structures which can be prepared by coprecipitation or via cogels (see, for example, Ind. Eng., Chem. Res. 34, 421.33 (1995); J. F. Harrod and R. M. Laine, Applications of Organometallic Chemistry in the Preparation and Processing of Advanced Materials, Kluver Academic Publishers (1995), pp.27–46) and zeolites, e.g. those of the structure types $\Omega$, X and L. Possible mobile ions in these zeolites are, for example, the elements of main groups 1, 2 and 3 and of transition group 3 of the Periodic Table of the Elements and the rare earths. Preference is given to H, Na, K, Rb, Cs, Ca, Mg, Sr, Ba, Sc, Y, La, Ce and Pr. Particularly preferred ring-chlorination catalysts are zeolites of the structure type L, very particularly preferably of the type K-L in which the mobile ions are from 80 to 100%, preferably from 90 to 100%, potassium ions.

The ring-chlorination catalyst can be used, for example, in amounts of from 0.2 to 20% by weight, preferably in amounts of from 2 to 12% by weight, based on biphenyl used.

The reaction according to the invention can be carried out at, for example, temperatures of from 0 to 120° C., preferably temperatures of from 20 to 100° C. The pressure during the reaction according to the invention is not critical and can be, for example, from 0.2 to 20 bar. It is preferably from 0.8 to 8 bar. Particular preference is given to carrying out the chlorination at atmospheric pressure.

The reaction according to the invention can be carried out batchwise, semibatchwise or continuously. Suitable batch reactors are, for example, stirred vessels, bubble columns and loop reactors. If the process is to be carried out continuously, this can be achieved by connecting a plurality of the abovementioned batch reactors in series. In principle, however, it is also possible to use residence tube reactors or reactors employing stationary catalyst beds.

The reaction according to the invention can be carried out in the presence or absence of a solvent and/or a cocatalyst. Suitable solvents are, for example, aprotic solvents which do not react with chlorine under the reaction conditions. Preference is given to chlorinated hydrocarbons, in particular methylene chloride. A suitable cocatalyst is, for example, chloroacetic acid. The chlorination according to the invention is generally carried out in such a way that from 30 to 90%, preferably from 10 to 70%, particularly preferably from 30 to 60%, of the biphenyl used are reacted in a single pass.

In the process of the invention, the reaction mixture present after the chlorination is separated into its components exclusively by means of a fractional distillation.

If a heterogeneous ring-chlorination catalyst, e.g. a zeolite, has been used, this is advantageously separated off mechanically, e.g. by filtration or centrifugation, prior to the distillation. If a soluble ring-chlorination catalyst such as iron trichloride has been used, this is advantageously deactivated and separated off, e.g. by addition of water and removal of the aqueous phase, prior to the distillation.

Before the distillation, a base can be added to the mixture to be distilled in order to destroy any residues having a catalytic activity and thus reliably to prevent transchlorinations during the distillation. Suitable bases for this purpose are, for example, sodium carbonate, calcium carbonate, sodium acetate and potassium hydrogencarbonate.

The columns for the fractionation of the reaction mixture from the chlorination, which may have been pretreated as described above, can have, for example, from 5 to 500, preferably from 10 to 100, particularly preferably from 20 to 50, theoretical plates. The manner in which this number of theoretical plates can be achieved by means of internals in the column is known to those skilled in the art. The columns are, for example, operated at a reflux ratio of from 1 to 30, preferably from 2 to 20.

The columns can be operated, for example, at temperatures at the bottom of from 100 to 300° C., preferably from 150 to 250° C., and at pressures beginning in the range from 0.5 to 3 bar and ending in the range from 3 to 300 mbar, preferably from 10 to 100 mbar.

The fractional distillation can be carried out batchwise, semibatchwise or continuously.

A continuous fractional distillation process can be carried out using, for example, three columns which are connected in series and are each equipped with stripping sections and enrichment sections. The first column gives unreacted biphenyl at the top, the second gives 2-chlorobiphenyl at the top and the third gives 4-chlorobiphenyl at the top.

A batchwise fractional distillation can be carried out using a column of the above-described type which is not equipped with a stripping section and an enrichment section.

If a solvent, e.g. methylene chloride, has been used, this is advantageously separated off before the actual fractional distillation, e.g. by distillation in a column installed upstream.

The chlorination according to the invention generally leads to reaction mixtures containing little 3-chlorobiphenyl. The ratio of 4-chlorobiphenyl to 3-chlorobiphenyl in the reaction mixture is, for example, above 100:1, frequently above 300:1 and particularly advantageously above 800:1. If it is, in an exceptional case, 100:1 or below, routine tests should be carried out to find a combination of reaction conditions, catalyst and possibly solvent in the case of which the desired low contents of 3-chlorobiphenyl can be obtained in the reaction mixture. The fractional distillation to be carried out according to the invention thus always makes it possible for the 3-chlorobiphenyl content of the 4-chlorobiphenyl isolated to be reduced appreciably in this way, even though the reduction may not be to below the detection limit.

Furthermore, the process of the invention makes it possible to obtain 4-chlorobiphenyl having a purity of 99.5% or more, frequently 99.95% or more, in a simple manner from simple starting materials and using simple auxiliaries. It is thus well suited for further processing to produce pharmaceuticals and crop protection products. The yields of 4-chlorobiphenyl in the process of the invention are above 90%.

The process of the invention has for the first time made available 4-chlorobiphenyl containing from 0.001 to 10‰, preferably from 0.01 to 1‰ and particularly preferably from 0.03 to 0.3‰, of 3-chlorobiphenyl. It is a typical feature of the process of the invention that it gives 4-chlorobiphenyl having these 3-chlorobiphenyl contents.

The present invention therefore also provides 4-chlorobiphenyl containing from 0.001 to 10‰, preferably from 0.01 to 1‰, particularly preferably from 0.03 to 0.3‰, of 3-chlorobiphenyl.

EXAMPLES

General a) For the quantitative determination of the components, 5% strength solutions of the reaction mixtures in chlorobenzene were analyzed by gas chromatography.

The detection limits were: 200 ppm of biphenyl, 100 ppm of monochlorobiphenyl, 400 ppm of 4,4'-dichlorobiphenyl and 400 ppm of trichlorobiphenyls.

b) Reactor: oil-thermostated 250 ml flange pot with gas inlet tube and stirrer.

Example 1

Chlorination in Methylene Chloride 93.5 g of biphenyl together with 134 g of methylene chloride were placed in the reactor and 9 g of zeolite of the type K-L (dry) were added as a fine powder. The reactor was flushed with nitrogen and introduction of chlorine was commenced at 40° C. Details may be found in Table 1.

TABLE 1

| Time of chlorine introduction (min) | Amount of chlorine | Content in the reaction mixture (% by area) | | | | | Selectivity to 4-chlorobiphenyl (%) |
|---|---|---|---|---|---|---|---|
| | | Biphenyl | Chlorobiphenyl | | | | |
| | | | 2- | 3- | 4- | 4,4'-di | |
| 45 | 28.7 | 76.92 | 0.74 | 0.01 | 21.59 | 0.58 | 93.54 |
| 80 | 47.2 | 61.33 | 1.21 | 0.04 | 35.29 | 1.83 | 91.26 |
| 108 | 62.8 | 48.94 | 1.58 | 0.04 | 45.46 | 3.60 | 90.34 |
| 125 | 70.5 | 43.22 | 1.76 | 0.06 | 49.79 | 4.74 | 87.69 |

Example 2

Chlorination in the Presence of Chloroacetic Acid 101 g of biphenyl, 2.5 g of chloroacetic acid and 10 g of zeolite of the type K-L (dry) were placed in the reactor and the reactor was flushed with nitrogen. The mixture was then heated to 100° C. and the introduction of chlorine was commenced. Details may be found in Table 2.

TABLE 2

| Time of chlorine introduction (min) | Amount of chlorine | Content in the reaction mixture (% by area) | | | | | Selectivity to 4-chlorobiphenyl (%) |
|---|---|---|---|---|---|---|---|
| | | Biphenyl | 2- | 3- | 4- | 4,4'-di | |
| 240 | 31.8 | 79.55 | 2.51 | 0.08 | 16.07 | 0.31 | 78.58 |
| 425 | 58.7 | 59.75 | 5.41 | 0.12 | 30.03 | 1.27 | 74.61 |

Example 3
Distillation (all Percentages are by Weight Unless Indicated Otherwise; CBP Represents Chlorobiphenyl).

The procedure of Example 1 was used to prepare a larger amount of reaction mixture having the composition present in Example 1 after a chlorination time of 108 minutes. The catalyst was firstly removed from this reaction mixture by filtration and the major part of the methylene chloride was taken off via a column. This left 2991.5 g of a mixture comprising 7.45% of methylene chloride,
45.86% of biphenyl,
1.62% of 2-CBP,
0.12% of 3-CBP,
41.5% of 4-CBP and
3.44% of 4,4'-DICBP.

This mixture was fractionally distilled from a 4 l flask as still pot via a column having 34 theoretical plates (internal diameter: 5 cm, height: 100 cm, packing: 4×4 mm wire mesh rings).

Firstly, 56.8 g of methylene chloride were obtained at atmospheric pressure and a pressure reduced down to 500 mbar, at temperatures at the bottom of from 202 to 210° C., temperatures at the top of from 39 to 24° C. and a reflux ratio of 5.

Subsequently, 1209.4 g of biphenyl were obtained at a pressure at the top of the column of 30 mbar, at temperatures at the bottom of from 156 to 178° C., at temperatures at the top of 136–137° C. and a reflux ratio of 5. This can be returned to the chlorination.

254.9 g of an intermediate fraction comprising biphenyl, 2-CBP, 3-CBP and 4-CBP were then obtained at a pressure at the top of the column of 30 mbar, at temperatures at the bottom of from 178 to 179° C., temperatures at the top of from 138 to 166° C. and a reflux ratio rising from 5 to 10. This fraction can be returned to the distillation.

Now, 351.6 g of a first 4-CBP fraction comprising 99.7% of 4-CBP, 0.16% of 3-CBP and less than 0.1% of 2-CBP and less than 0.1% of biphenyl were obtained at a pressure at the top of the column of 30 mbar, a temperature at the bottom of 180° C., a temperature at the top of 166° C. and a reflux ratio of 10. This fraction can, if the specification is satisfactory, be passed on as product, if appropriate in admixture with the second 4-CBP fraction, or, if the specification is not satisfactory, be returned to the distillation.

Finally, 675.5 g of a second 4-CBP fraction comprising above 99.95% of 4-CBP and 0.03% of 3-CBP were obtained at a pressure at the top of the column of 30 mbar, temperatures at the bottom of from 181 to 231° C., a temperature at the top of 166° C. and a reflux ratio of 2.

What is claimed is:

1. A process for preparing 4-chlorobiphenyl containing from 0.001 to 10‰ of 3-chlorobiphenyl comprising
   (a) reacting biphenyl and chlorine in the presence of one or more ring-chlorination catalysts, and
   (b) subjecting the reaction mixture obtained in step (a) to fractional distillation to obtain 4-chlorobiphenyl.

2. A process according to claim 1 wherein the ring-chlorination catalyst is an anhydrous chloride of a metal of main groups 3, 4, or 5 and/or of transition groups 3 to 10 of the Periodic Table of the Elements, an anhydrous chloride of a rare earth metal, or an aluminosilicate.

3. A process according to claim 1 wherein the ring-chlorination catalyst is a zeolite of type L having mobile ions wherein 80 to 100% of the mobile ions are potassium ions.

4. A process according to claim 1 wherein the ring-chlorination catalyst is used in an amount of from 0.2 to 20% by weight, based on the biphenyl.

5. A process according to claim 1 carried out at temperatures of from 0 to 120° C. and pressures in the range from 0.2 to 20 bar.

6. A process according to claim 1 carried out in such a way that from 30 to 90% of the biphenyl is reacted in a single pass.

7. A process according to claim 1 wherein the fractional distillation is carried out using a column having from 5 to 500 theoretical plates and operated at a reflux ratio in the range from 1 to 30.

8. A process according to claim 1 wherein the reaction and the fractional distillation steps are, independently of one another, carried out batchwise, semibatchwise, or continuously.

9. 4-Chlorobiphenyl containing from 0.001 to 10‰ of 3-chlorobiphenyl.

10. 4-Chlorobiphenyl according to claim 9 containing from 0.001 to 1‰ of 3-chlorobiphenyl.

\* \* \* \* \*